(12) United States Patent
Janssen et al.

(10) Patent No.: US 9,341,574 B2
(45) Date of Patent: May 17, 2016

(54) RAMAN SPECTROMETER, SENSOR ELEMENT FOR A RAMAN SPECTROMETER AND A METHOD FOR OBTAINING A RAMAN SPECTRUM USING THE SENSOR ELEMENT

(75) Inventors: Kjeld Gertrudus Hendrikus Janssen, Afferden (NL); Thomas Hankemeier, Leiden (NL)

(73) Assignee: UNIVERSITEIT LEIDEN, Leiden (NL)

( * ) Notice: Subject to any disclaimer, the term of this patent is extended or adjusted under 35 U.S.C. 154(b) by 181 days.

(21) Appl. No.: 13/580,392

(22) PCT Filed: Feb. 22, 2011

(86) PCT No.: PCT/NL2011/050124
§ 371 (c)(1),
(2), (4) Date: Oct. 24, 2012

(87) PCT Pub. No.: WO2011/102728
PCT Pub. Date: Aug. 25, 2011

(65) Prior Publication Data
US 2013/0050694 A1 Feb. 28, 2013

(30) Foreign Application Priority Data
Feb. 22, 2010 (NL) .................................. 2004275

(51) Int. Cl.
*G01J 3/44* (2006.01)
*B05D 5/12* (2006.01)
(Continued)

(52) U.S. Cl.
CPC ............ *G01N 21/658* (2013.01); *G01N 21/648* (2013.01); *G01N 21/7703* (2013.01); *G01N 2021/6484* (2013.01); *G01N 2021/772* (2013.01)

(58) Field of Classification Search
CPC ................ G01N 21/65; G01N 21/658; G01N 2021/6484; G01N 2021/772; G01N 21/648; G01N 21/7703; G01J 3/44
USPC ......................................................... 356/301
See application file for complete search history.

(56) References Cited

U.S. PATENT DOCUMENTS 5,266,498 A 11/1993 Tarcha et al.
5,327,211 A 7/1994 Carron et al.
(Continued)

FOREIGN PATENT DOCUMENTS

WO WO 2005/111559 A2 11/2005

OTHER PUBLICATIONS

J. DeSaja-Gonzaleza, R. Aroca, Y. Nagaob, J.A DeSajac, "Surface-enhanced fluorescence and SERRS spectra of N-octadecyl-3,4:9,10-perylenetetracarboxylic monoanhydride on silver island films," (1997), Spectrochimica Acta Part A 53, 173-181.*
(Continued)

*Primary Examiner* — Kara E Geisel
*Assistant Examiner* — Violeta A Prieto
(74) *Attorney, Agent, or Firm* — Hoffmann & Baron LLP

(57) ABSTRACT

A Raman spectrometer includes a light source (12), a sensor element (14) and a detector (10), where the sensor element (14) includes an active surface (24), which active surface (24) is coated with a layer (26) of inert material to be placed in contact with the sample (4). A sensor element (14) includes an active surface (24) which is coated with a layer (26) of inert material. A method for obtaining a Raman spectrum using such a sensor element (14) includes the following steps: a) providing a sensor element (14), comprising an active surface (24) which is coated with a layer (26) of inert material and placing the layer (26) of inert material in contact with a sample to be analysed; b) illuminating the sensor element (14) with monochromatic light; and c) detecting surface enhanced Raman scattering by the sensor element (14).

39 Claims, 2 Drawing Sheets

(51) Int. Cl.
*G01N 21/64* (2006.01)
*G01N 21/65* (2006.01)
*G01N 21/77* (2006.01)

(56) References Cited

U.S. PATENT DOCUMENTS

| | | | |
|---|---|---|---|
| 5,721,102 A | | 2/1998 | Vo-Dinh |
| 5,783,389 A | * | 7/1998 | Vo-Dinh ................ 435/6.12 |
| 5,814,516 A | * | 9/1998 | Vo-Dinh ................ 435/287.2 |
| 6,623,977 B1 | | 9/2003 | Farquharson et al. |
| 6,858,713 B1 | * | 2/2005 | Bradley et al. ................ 506/15 |
| 7,142,296 B2 | * | 11/2006 | Cunningham et al. ........ 356/326 |
| 7,158,230 B2 | * | 1/2007 | Cunningham et al. ........ 356/326 |
| 7,560,285 B2 | * | 7/2009 | Sun ................ 436/164 |
| 2005/0148101 A1 | * | 7/2005 | Bamdad et al. ................ 436/524 |
| 2005/0217424 A1 | | 10/2005 | Natan |
| 2006/0147927 A1 | | 7/2006 | Geddes et al. |
| 2007/0020144 A1 | | 1/2007 | Du et al. |
| 2008/0074661 A1 | | 3/2008 | Zhang et al. |
| 2008/0285024 A1 | | 11/2008 | Prokes et al. |
| 2009/0213369 A1 | | 8/2009 | Lee et al. |
| 2009/0257056 A1 | * | 10/2009 | Demirel et al. ................ 356/301 |
| 2011/0007308 A1 | * | 1/2011 | Fong et al. ................ 356/301 |
| 2012/0127465 A1 | * | 5/2012 | Piorek et al. ................ 356/301 |

OTHER PUBLICATIONS

EPO Communication for a counterpart foreign application dated Sep. 30, 2014.

\* cited by examiner

RAMAN SPECTROMETER, SENSOR ELEMENT FOR A RAMAN SPECTROMETER AND A METHOD FOR OBTAINING A RAMAN SPECTRUM USING THE SENSOR ELEMENT

CROSS-REFERENCE TO RELATED APPLICATIONS

This application is the National Stage of International Application No. PCT/NL2011/050124, filed Feb. 22, 2011, which claims the benefit of Netherlands Application No. 2004275, filed Feb. 22, 2010, the contents of which is incorporated by reference herein.

FIELD OF THE INVENTION

The invention relates to a Raman spectrometer, a sensor element suitable for a Raman spectrometer and to a method for obtaining a Raman spectrum using the sensor element. The invention further relates to a method for manufacturing a sensor element and the use of a sensor element.

BACKGROUND OF THE INVENTION

The inelastic scattering of photons is called the Raman effect, where Rayleigh scattering refers to elastic scattering. The measurement and analysis of the signals (photons) arising from the Raman effect is called Raman spectroscopy, see D. A. Long, "The Raman effect, unified treatment of the theory of Raman scattering by molecules", John Wiley & Sons Ltd., Chichester, 2002.

A measurement device for this purpose is termed a Raman spectrometer and can be used for studying vibrational, rotational, and/or other low-frequency modes in a system, see for instance W. Demtröder, "Laser Spectroscopy", Springer, Berlin, 2002, and "Practical Raman spectrometry" by D. J. Gardiner, Springer-Verlag, 1989.

A Raman spectrometer commonly provides a spectrum, i.e. a Raman spectrum, of intensities associated with frequency shifts with respect to incident monochromatic radiation resulting from the Raman effect. Since vibrational information is specific to the chemical bonds of molecules, the Raman spectrum provides a fingerprint by which the molecules (hereinafter referred to as analytes) can be identified. In addition, Raman spectroscopy is a potentially quantitative technique and dynamic measurements of chemical processes and interactions are possible. These features make it a useful tool in chemistry.

An example of a Raman spectrometer can be found in the international publication WO 2005/111559. A Raman spectrometer comprises a light source to illuminate a sample usually with monochromatic light, and a detector to detect Raman scattering of the illuminated sample. Optical systems are provided to direct light from the light source to the sample, to collect the scattered light, and to direct the collected scattered light to the detector.

Monochromatic light refers to electromagnetic radiation of a single wavelength. However, in practice, no real source of electromagnetic radiation is purely monochromatic. Therefore, monochromatic light also refers to sources that have a narrow range of wavelengths, such as lasers in which the narrow range of wavelengths is sometimes also referred to as spectral line width. It is noted here that the term light not necessarily refers to radiation having a wavelength in the visible range. Also wavelengths outside this range, such as infrared light, can be used. It is stated that the phenomenon of Raman scattered light is useful in spectroscopy applications for studying qualities and quantities of physical properties and processes, including identification of chemical properties, compositions, and structure in a sample.

The main problem with the acquisition of a Raman spectrum is that Raman scattering is relatively weak compared to elastic Rayleigh scattering, as a result of which the detection limit of this measurement technique is relatively poor.

The detection limit is the lowest quantity of an analyte in a sample to be measured that can be distinguished from the absence of that analyte.

An approach to improve the detection limit is filtering out the Rayleigh scattering using an appropriate filter. However, even when all Rayleigh scattering would be filtered out, the detection limit is often too poor to allow the measurement of small quantities of the analyte.

To overcome this drawback Surface Enhanced Raman Spectroscopy was developed. Surface Enhanced Raman Spectroscopy, or Surface Enhanced Raman Scattering, often abbreviated SERS, is a surface-sensitive technique that enhances Raman scattering by molecules adsorbed on rough surfaces. The principle of using a roughened SERS active surface (hereinafter referred to as 'active surface') to enhance Raman scattering is known to a person skilled in the art. SERS is a technique used to improve the detection limit for Raman measurements, commonly by deliberately targeting the molecule, i.e. the substance or analyte of interest. Targeting the molecule can be done directly by the active surface, wherein the preference of the active surface to adsorb or bond with specific substances or parts thereof is used to enrich the analyte in close proximity of the active surface. Targeting can also be done via an intermediate layer which is covering the active substrate and has a preference to adsorb or bond with specific substances or parts thereof to get the analyte in close proximity of the active surface. It is also possible that the intermediate layer does target the analyte but not for the specific purpose to get it into close proximity. In such occasions when the analyte adheres to or bonds with the intermediate layer, properties of the intermediate layer change. As the intermediate layer itself is in close proximity of the active surface, the change in properties can be measured, thereby indirectly detecting the analyte.

An advantage of targeting the molecules may be that the concentration of the substance to be measured is increased near the active surface with respect to the concentration in the analyte, and thereby also increases the enhanced Raman signal due to the substance.

By getting the substances as close to the active surface as possible, i.e. directly or indirectly, the enhancement factor of the active surface may be such that even single molecules can be detected under specific conditions. However, the technique can not be used to perform subsequent measurements of substances, as the bonding or adsorption of the substances in SERS is generally irreversible, so that a measurement will influence and/or foul a next measurement. Sensor elements in SERS are thus used for so-called one-shot measurements only. Due to this feature, a disadvantage of this technique is that it does not allow dynamic measurements, thereby limiting the possibility of calibration and quantitative measurements.

Further techniques have been developed to enhance the signal. One such technique has been to enhance the concentration of the analyte close to the surface that is being illuminated. An example therefore is to apply the so-called drop and drying technique which involves dropping or pipetting small volumes, e.g. about 1-20 µl, of an analyte solutions onto an active surface, e.g., a gold active surface, and allowing the analyte to dry. By this method remaining analyte after drying is provided as close to the active surface as possible. In addition, the gold tends to have a great affinity to the analyte, binding it firmly. Another example has been described in U.S. Pat. No. 5,721,102. This document describes a Raman spectrometer comprising a light source, an active substrate containing the analyte, and a detector. The active substrate was prepared by depositing a layer of silver with a thickness of 100 nm onto a glass strip. The silver layer was coated by a layer of e.g., silica or an organic polymer, wherein an oligonucleotide of known sequence was immobilised. The known oligonucleotide was complementary to the target oligonucleotide, which is the analyte. The analyte and the known oligonucleotide are allowed to hybridise, so that an enhanced concentration of the analyte is present at the active substrate. In US 2006/0147927 a similar technique is described; polynucleotides are attached to a surface having silver colloids and/or silver islands. The polynucleotides are complementary to a target polynucleotide sequence. The target nucleotide sequence is added to the surface and the target is allowed to hybridise.

U.S. Pat. No. 5,266,498 discloses a SERS method wherein an active surface is provided with a binding member that is bound to the active surface. The binding member has an affinity for the analyte or an indicator reagent. Upon binding of the analyte the change in the Raman signal of the binding member facilitates the detection of the analyte. In US 2005/0219509 a Raman technique is described in which the active surface and the analyte are associated with each other. Subsequently they are surrounded by an encapsulant. Such encapsulation ensures that only the Raman scattering of the analytes on the active surface will be detected.

The above-described techniques have the advantage that they concentrate the molecules to be detected in close proximity to the active surface. However, these techniques have the disadvantage that each measurement must be conducted on a separate active substrate, which adds to costs and effort. Further, these techniques render quantitative determinations very cumbersome. Moreover, these techniques cannot be used in an on-line measurement or in a dynamic determination in order to follow processes. Finally, due to their specificity they may not be suitable for the detection of unknown compounds.

Hence, whereas conventional Raman spectroscopy has the disadvantage of a weak signal, the above SERS techniques have the disadvantages that quantitative analyses and dynamic measurements are virtually impossible.

SUMMARY OF THE INVENTION

It is therefore an object of the invention to provide a Raman spectrometer with an improved detection limit that allows dynamic and quantitative measurements.

This object is achieved by a Raman spectrometer which comprises a light source, a sensor element and a detector, wherein the sensor element comprises an active surface, which active surface is coated with a layer of inert material to be placed in contact with a sample to be analysed.

Preferably, said layer of inert material is thin enough to allow surface enhanced Raman scattering of the analyte when said analyte is in close proximity to the active surface. The inert material does not bind with the analyte or does not attract the analyte. The inert material does not have a tendency for bonding with, adhering to or adsorbing the analyte.

An advantage of the Raman spectrometer according to the invention is that the Raman scattering of the analyte is enhanced by the active surface, thereby increasing the intensity of the Raman scattering and thus the detection limit. Moreover, since the layer of inert material on the one hand allows the analyte to come in close proximity with the active surface, but on the other hand is inert to the analyte, the analyte does not bind and is therefore also removed from the sensor element. In this way it is possible to conduct quantitative and dynamic measurements, and/or to easily clean the sensor element.

A sample may comprise one or more compounds, wherein each compound can be present in the gas, liquid or solid phase, or a part thereof. For example, the sample comprises a compound present in a solution or a mixture. At least one compound is the analyte, i.e. compound of interest. Other compounds which are present but not of interest, e.g. solvent, are referred to as background compounds. It is also possible that the sample comprises multiple compounds of interest, i.e. analytes. When in this application reference is made to analyte, this also includes the possibility of multiple analytes if appropriate. The sample may also be part of the gaseous and liquid phase at the same time, wherein the sensor element can be provided at the boundary of the gas and liquid phase and measure both phases at the same time. Preferably, the sample is brought into contact with the sensor element during measurements. More preferably, the sample is brought into contact with the layer of inert material.

The analytes may be selected from a wide range of chemicals. The skilled person will know what molecules give a relevant signal in Raman scattering. The present invention can advantageously be applied in the determination of drugs, medicaments, metabolites of drugs of medicaments, proteins, peptides, polynucleotides, endogenous and non-endogenous metabolites in general. Further many other chemicals are also suitable for detection with the spectrometer according to the present invention. Since many compounds can be used as analytes in the present invention this may have as a result that a certain layer of inert material is not perfectly inert to some of the compounds that are contained in a sample. The skilled person will realise that when a sample is complex and contains too many compounds that will provoke a Raman signal sample preparation and/or data analysis methods may be recommendable.

An additional advantage of the invention may be that the layer of inert material covering the active surface ensures, due to its inertness to the analyte, that the portion of the analyte which is in close proximity to the active surface is a substantially true representation of the concentration of the analyte, i.e. not intentionally biased. The layer of inert material thus does not have a preference for bonding with or adhering to the analyte, which preference would negatively affect a quantitative measurement, and thus still allows the Raman spectrometer to be used for both quantitative and qualitative measurements.

Preferably, the interaction between layer of material and analyte of interest is kept to a minimum when choosing the layer of material. The composition of the layer of inert material can thus be an important design factor for the analyses of a given analyte.

The inertness of the layer of material also allows rinsing and cleaning of the layer of inert material so that molecules which were inadvertently deposited or have precipitated unto the layer of material can easily be removed and a new measurement can be started, thereby ensuring that subsequent measurements do not have an influence on each other. Preferably such influence is eliminated completely although that may not be achieved due to practical reasons associated with rinsing and cleaning and/or the analyte or background compounds involved.

Preferably, in case of multiple analytes, the layer of inert material is inert to more than one analyte, preferably all analytes. Preferably, the layer of inert material is also inert to substances in the sample other than the analyte, i.e. the background compounds. More preferably, the layer of inert material is inert to all substances in the sample.

In an embodiment, the spectrometer can be used for dynamic measurements of its environment in for instance process monitoring of an analyte of interest or as an in-line sensor in separation sciences.

The use of the sensor to measure an analyte of interest in solution while a precursor or different state (including pH dependency) of the analyte binds to the layer of material is also considered to fall within the scope of the invention. For example, said binding is intentional while the release or formation of the analyte of interest is measured.

The mechanism behind the enhancement of Raman scattering by an active surface can be found in "Surface Enhanced Raman Scattering, Physics and Applications", by Kneipp, K., Moskovits, M., and Kneipp, H., Springer-Verlag Berlin Heidelberg, 2006, and "Principles of Surface-Enhanced Raman Spectroscopy and related plasmonic effects" by Le Ru, E. C., and Etchegoin, P. G., Elsevier, 2009.

Usually the active surface comprises a metal, such as silver, gold, copper, platinum, palladium and cobalt, but also graphene can be used. Certain alloys and composites are known to be able to enhance Raman scattering. It is preferred that the active surface consists of gold and/or silver. It is also possible that the active surface comprises a bilayer or multilayer, e.g. gold and silver. The active surface may in other documents be referred to as active layer, active substrate, active element, etc. as known to the person skilled in the art of SERS.

For the enhancing effect it has been found that the active surface has to have roughness features in the range of 1-1000 nm, preferably in the range of 30-150 nm. These features can be provided by roughening a surface, e.g. electrochemically, or by depositing nanoparticles, e.g. colloids, or nanostructures, e.g. nanowires, wherein the nanoparticles or nanostructures themselves not necessarily have to be rough, but the mutual orientation of multiple nanoparticles or nanostructures may form the active surface. In addition, a single nanoparticle, e.g. a colloid, which has a dimension in the earlier mentioned feature size range of 1-1000 nm, preferably in the range of 30-150 nm, may, due to its size, also be able to enhance Raman scattering and thus form an active surface according to the invention. Also, a rough surface of a carrier may be coated with a suitable material to form an active surface, wherein the desired feature size is obtained by the rough surface of the carrier. In fact any surface able to enhance Raman scattering, i.e. by a factor more than 1, preferably more than 10, more preferably more than 1000, most preferably more than 100.000, compared to the situation in which the active surface is absent, can form the basis for an active surface according to the invention.

It is mentioned here that the ideal feature size of the active surface highly depends on the wavelength of the monochromatic light used to illuminate the analyte. The persons skilled in the art will realise that bigger features operate better at longer wavelengths.

The actual amount of enhancement of the Raman scattering by the active surface is also dependent on the distance of the analyte with respect to the active surface. In fact, the amount of enhancement decreases with increasing distance. The analyte is therefore preferably as close to the active surface as possible, or in other words, the layer of inert material is preferably as thin as possible to allow molecules in the analyte to get into close proximity of the active surface, so that the active surface is able to enhance the Raman scattering of the molecules.

Therefore, the layer of inert material preferably has a thickness such that Raman scattering of analytes in a sample can be enhanced by more than 1, preferably more than 10, more preferably more than 1000, most preferably more than 100.000 times, with respect to the situation where the active surface with coating is absent, i.e. the sensor element is absent. The thickness of the layer of material is preferably in the order of a few nanometers or tens of nanometers, viz. less than 50 nm, preferably from 0.1 to 20, more preferably from 0.1 to 5 nm. The layer of inert material might be a monolayer. By monolayer is understood a layer with a thickness of one molecule.

In an embodiment, the spectrometer according to the invention is in particular useful to analyse analytes which are not inert to the active surface itself. Due to the inert layer such analytes will have no tendency to bind, adhere or adsorb to the active surface, whereby it is enabled to conduct quantitative and in-line measurements. Such measurements would not have been able if such analytes would be attracted to the active surface and bound to it.

The layer of inert material is inert to the analyte. In an embodiment the inert layer is composed of molecules that by themselves may not have to be inert, for instance when they are in a solution. However, at least after providing the molecules on the active surface as the coating, the layer of inert material is inert to the analyte, which means that the side of the layer of material facing away from the active surface is inert. The side of the layer of material facing the active surface may not be inert, which can advantageously be used to provide the necessary adherence between active surface and layer of material. This property can also be used to orient the molecules in the layer of material, preferably such that they all have the same orientation to form a homogenous layer. As an example, molecules can be used that contain thiol or amine groups that tend to bind to a metal active surface, e.g., gold or silver. The remainder of the molecule may subsequently be part of the inert layer.

In an embodiment the layer is not inert when it is applied to the active surface, but is subsequently modified to become inert. For example, the layer is modified by a chemical reaction to remove non-inert groups or to react with molecules such that the layer becomes inert.

In an embodiment, the layer of inert material forms a dynamic coating as understood by a person skilled in the art of surface coating chemistry, in which molecules of the layer of material may be present in a solution near the active surface and other molecules of the layer of material may adhere to the active surface at the same time, wherein individual molecules may alternating be present in the solution and on the active surface, but the overall properties of the coating are substantially constant. In this embodiment, it is also envisaged that measurements are performed by allowing the analyte temporarily access to the surface, where after it is displaced by a molecule of the layer of material again such that the signal reflects the concentration of the analyte. Preferably, the layer of inert material is immobilized on the active surface.

In an embodiment, the layer of inert material is composed of two or more sub-layers. For example, a sub-layer to increase adhesion between the active surface and an outer inert sub-layer to provide the inertness of the layer as a whole with respect to the analyte. It is also possible that one sub-layer is immobilized, and another sub-layer is a dynamic coating. It is mentioned here that in case multiple layers are present on the active surface, the outer layer, i.e. the one forming at least partially the outer surface of the sensor element, is preferably the layer being inert to the analyte of interest.

In an embodiment, the layer of inert material, or possibly the sub-layers, is/are heterogeneous with respect to their molecular composition. Hereby is understood that the layer or sub-layers, as the case may be, are organic compounds containing a hetero atom. An example of such a compounds is ethanethiol.

The layer of inert material may be suitably selected from the group consisting of inorganic materials, such as glass, silica, silicon nitride or alumina, and organic polymers. Preferably, the layer of inert material comprises a polymer selected from the group consisting of carnauba wax, ethyl cellulose, ethylene maleic anhydride copolymer, methyl vinyl ether, octadecyl vinyl ether, phenoxy resin, poly 2-ethylhexyl methacrylate, poly (caprolactone), poly (caprolactone) triol, polybutadiene, poly-n-butyl acrylate, poly-p-vinyl phenol, polybutadiene oxide, polybutadiene hydroxy terminated, polybutadiene-methylacrylated, polybutadiene acrylonitrile, polydecyl acetate, polyethyl acrylate, polyethylene, polyethylene glycol methyl ether, polyethylene glycol, polyhexyl methacrylate, poly-1-butene, polymethacrylate, polystyrene, polyvinyl butyryl, polyvinyl carbazone, polyvinyl chloride, polyvinyl isobutyl ether, polyvinyl methyl ether, polyvinyl stearate, and vinyl alcohol/vinyl acetate copolymer. Also fluorinated polymers may be used, such as poly tetrafluoroethylene. It has been found that these polymers are very suitable since the bonds between carbon, hydrogen and oxygen tend to give little Raman scattering whereas they are also inert vis-à-vis compounds containing groups with a significant Raman effect. Very good results have been obtained with polyethylene glycol layers.

In an embodiment, the layer of inert material is attached to the active surface, preferably via a binding unit e.g. thiol or amine. In a preferred embodiment, the layer of inert material comprises polyethylene glycol thiol, whereby the thiol group attaches the polyethylene chain to the metal of the active surface.

The end group of molecules used in the layer of inert material, such as for instance the SH group of polyethylene glycol thiol may be chosen for its adherence to the active surface, or for the orientation it gives to the remainder of the molecule when adhered to the active surface. This orientation of the molecules may determine the thickness and inertness of the layer of material and can therefore be an important design factor.

As the active surface may have a preference for a particular substance or part thereof, the active surface may be encapsulated to prevent direct contact between the active surface and the analyte. At least part of the encapsulation is formed by the layer of inert material covering the active surface, but it is also envisaged that encapsulation is partially provided by another material or additional layer on top of the layer of inert material. Such may be convenient if the sensor element is used for first identifying whether a particular analyte is present for which the uncoated part of the active surface and/or the additional layer may be used, and subsequently proceed with dynamic measurements, for which the layer of inert material is used. If the material forming the active surface is thick enough, this may also be considered to be encapsulating the active surface as it protects the analyte from getting close to the active surface from the other side than the layer of material.

Due to differences in size of compounds, the encapsulation for the analyte does not necessarily mean that other compounds, i.e. the background compounds, are also not able to reach the active surface. However, it may be preferred that contact between the active surface and the entire sample is prevented. It can be an important design factor.

In an embodiment, the sensor element can have different areas for different functionality. It is therefore possible that the same layer of inert material is not covering the entire active surface, and one or more different inert material layers cover other portions of the active surface. By measuring different areas of the sensor element, it is possible to switch between functions of the sensor element, thereby allowing dynamic measurements on one layer of material, and one-shot and/or selective measurements using another layer of material. For instance, it is possible to provide a sensor element which can be used to determine the moment of creation of a certain molecule in a reaction by using SERS techniques that detect the presence of said molecule at an early stage, i.e. by single molecule detection, and this measurement triggers the dynamic measurement of another substance, e.g. concentration, using the area with the layer of material according to the invention, i.e. with the layer of material which is inert to the analyte.

In an embodiment, the spectrometer comprises a light source to illuminate the analyte with monochromatic light. The light source may be formed by filtering a polychromatic radiation source, e.g. a lamp or laser, with a monochromatic filter.

In an embodiment, the monochromatic light corresponds to a resonant frequency of the analyte as used in surface enhanced resonance Raman spectroscopy (SERRS). This technique has been described in e.g. Peter Hildebrandt, Manfred Stockburger, J. Phys. Chem., 1984, 88 (24), pp 5935-5944.

In an embodiment, the spectrometer comprises a detector, i.e. a detection means or means for detection, for detecting Raman scattering of the analyte. In principle, the human eye can function as a detector, for instance by using a monochromatic filter which at least blocks light with the frequency of the monochromatic light. However, in most practical Raman spectrometers, the detector comprises a CCD (charge-coupled device) camera or similar detection device to measure the frequency or frequency shift and/or intensity of the Raman scattered light.

In an embodiment, the Raman spectrometer comprises an optical system to direct light from the light source to the analyte and/or the sensor element, so that surface enhanced Raman scattering may take place.

In an embodiment, the Raman spectrometer comprises an optical system to collect light scattered by the analyte and direct it to the detector. In this way, the amount of light incident to the detector is increased, thereby also improving the detection limit of the overall spectrometer.

Light scattered by the analyte will generally consist of Rayleigh scattering and Raman scattering. The Rayleigh scattering is preferably filtered out by an appropriate filter, so that only Raman scattering, or at least minimal Rayleigh scattering will hit the detector. The filter is preferably placed between the optical system collecting the light from the illuminated analyte and the detector.

In an embodiment, the scattered light is diffracted with the use of a grating so as to resolve the different wavelengths spatially before arriving at the detector, e.g. the diffracted light is projected on a CCD camera.

The invention also relates to a sensor element, comprising an active surface which is coated with a layer of inert material.

The sensor element may have one or more of the features already described for the sensor element in the Raman spectrometer according to the invention. The sensor element is especially suitable to be used in Raman spectroscopy, i.e. in a Raman spectrometer according to the invention.

An advantage of the sensor element according to the invention is that it is also able to be used in Surface Enhanced Fluorescence (SEF), which uses a similar enhancement principle, i.e. near-field coupling between the analyte and surface plasmons of the active surface as for Raman scattering. When the sensor element is used in SEF, the thickness of the layer of material is preferably such that the enhancement is substantially maximal for SEF, because there is an optimal distance between analyte particles and active surface for SEF which is not similar to the optimal distance for Raman scattering or SERS. For Raman scattering, the optimal distance is as close as possible, where for SEF the distance has a predetermined value and is in the order of a few nanometers or tens of nanometers, e.g. from 1 to 150 nm.

In an embodiment, the layer of inert material provides a means to maintain distance between the active surface and the fluorescent analyte. Preferably, the coating is designed such that it provides a distance optimal for SEF.

It is further envisaged that the sensor element is also used in other applications using the enhancement of signals by the plasmonic effect of the active surface, see for the plasmonic effect "Principle of Surface-Enhanced Raman Spectroscopy and related plasmonic effects", by Le Ru, E. C., and Etchegoin, P. G., Elsevier, 2009.

In an embodiment, the sensor element comprises a carrier for carrying the active surface and the layer of material. The active surface may be located directly on the carrier, but it is also possible that an intermediate layer is present between the carrier and the active surface, for instance to increase the adherence of the active surface to the carrier. The intermediate layer may comprise functionalities the improve the binding between the active surface material and the carrier material. Suitably, the intermediate layer comprise amino and alkoxysilane moieties. These moieties may suitably bind to the carrier via the silane groups and also attach the active surface material, such as silver of gold, with the amino groups. An example of a suitable compound for such an intermediate layer is 3-aminopropyl trimethoxy silane. In principle any material that allows for an active surface, i.e. usually a metal surface with rough features, can be used as carrier. The carrier is suitably a solid material such as glass, silica and silicon. Other suitable carriers include plastics, polymer articles and paper. In this way, the sensor element can easily be handled and it is easier to direct light from the light source to the sensor element when the location of the active surface is known with respect to the carrier. The carrier may also be made from the same material as the active surface, for instance in case of an electrode, wherein the electrode, i.e. the carrier, has an active surface of its own. It is also possible that the electrode is coated with another material to form the active surface, for instance the electrode is made of silver and a layer of gold or gold particles covers the electrode to form the active surface.

In addition, the surface geometry of the carrier can be used to induce or enhance the required geometry of the active surface.

Another example of a carrier is a fibre, in particular a light-conducting fibre, wherein at an end surface of the fibre the active surface and layer of inert material are provided, so that light coupled into another end of the fibre is automatically directed towards the active surface. The fibre then acts as the carrier for the active surface and acts as an optical system to direct light towards the analyte and active surface. Optical light-conducting fibers made of glass, quartz or plastic are well known in the art.

The invention also relates to a method for manufacturing a sensor element, comprising the steps:
  a) providing an active surface;
  b) coating the active surface with a layer of inert material.

Preferably said layer of inert material is thin enough to allow surface enhanced Raman scattering of the analyte when said analyte is in proximity to the active surface.

In an embodiment, the active surface is provided on a carrier.

The invention also relates to a method for obtaining the Raman spectrum of an analyte using a sensor element as described above, wherein the method comprises the following steps:
  a) providing a sensor element, comprising an active surface which is coated with a layer of inert material and placing the layer of inert material in contact with a sample to be analysed;
  b) illuminating the sensor element with monochromatic light;
  c) detecting surface enhanced Raman scattering by the sensor element.

In an embodiment, the analyte is contained in a sample, which can be a gas or liquid and can be a solution or mixture of substances, wherein the sensor element is submerged into or brought into contact with the sample to provide the sensor element in close proximity of the analyte.

In an embodiment the sensor element is brought into contact with the sample to provide the sensor element in close proximity of the analyte. When reference to sample is made it is understood that the sample can be comprised of two or more phases, e.g. liquid and gas phases. It is understood that an appropriate inert coating may or may not be the same in the each phase. For example the sensor element is partly submerged in a sample solution containing the analyte, with another part of the sensor element in contact with the gas phase next to the solution, such that measuring the different areas allows measurement of the analyte in both phases. Another example is a water and organic solvent phase, which may be immiscible, allowing measurement of the distribution and/or state of the analyte in both phases.

In an embodiment, information is obtained about the frequency content and the associated intensity of the detected Raman scattering. Frequency content can be the frequency of the Raman scattered light, but also the frequency shift with respect to the frequency of the monochromatic light.

In an embodiment, Rayleigh scattering of the analyte is filtered out before detecting the Raman scattering.

The invention also relates to the use of a sensor element as described above in a Raman spectrometer for dynamic measurements, i.e. measurements over time. Preferably, the sensor element is cleaned before a measurement to remove remainders, e.g. inadvertent remainders, of previous analytes or background compounds as much as possible.

The sensor element according to the invention may be used in process monitoring, for example in liquids or gases. It may also be employed as an in-line sensor with separations, or with the coating properties chosen accordingly as a sensor for harsh conditions, or in-vivo applications.

BRIEF DESCRIPTION OF THE DRAWINGS

The invention will now be described in a non-limiting way by reference to the accompanying drawings in which like reference numerals refer to like parts. In the drawings.

DETAILED DESCRIPTION OF THE INVENTION

Figure 1:
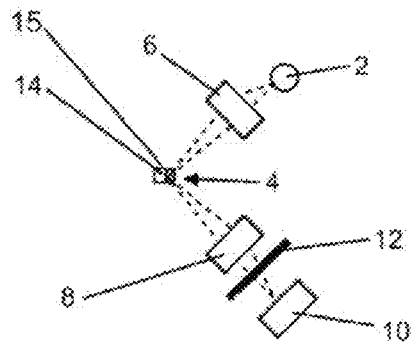
FIG. 1 depicts schematically a Raman spectrometer according to an embodiment of the invention.

FIG. 1 schematically depicts a Raman spectrometer according to an embodiment of the invention. The spectrometer comprises a light source 2 to illuminate a sample 4 with monochromatic light. Light is indicated in FIG. 1 by dashed lines. An optical system 6 in the form of a lens here focuses the light from the light source and directs it towards the sample 4 comprising a sensor element 14 and the analyte.

Surface enhanced Raman scattering of the analyte is collected by a further optical system 8, here also in the form of a lens which collects the light and directs it towards a detector 10. The Rayleigh scattering in the light is filtered out by a filter 12.

In the sample 4 the analyte is in close proximity of the sensor element 14. Sensor element 14 comprises an active surface which is coated with a layer of inert material 15, wherein said layer of material is thin enough to allow surface enhanced Raman scattering of the analyte such that Raman scattering of molecules in the analyte can be enhanced by more than 1, preferably more than 10, more preferably more than 1000, most preferably more than 100.000 times, with respect to the situation where the active surface with coating is absent, i.e. the sensor element is absent, when said analyte is in close proximity of the active surface, e.g. 0.1 to 20 nm. It is understood that preferably the closest proximity of the analyte corresponds with the actual thickness of the layer. The sensor element may consist of active surface and layer of inert material alone, but it is also possible that the metal and coating are provided on a carrier to make the sensor element easier to handle and the light spot of the light source easier to direct towards the analyte-containing sample. For example, the carrier may be the tip of a fibre. The light is directed both to the analyte and the active surface such that it allows surface enhanced Raman scattering.

Figure 2:
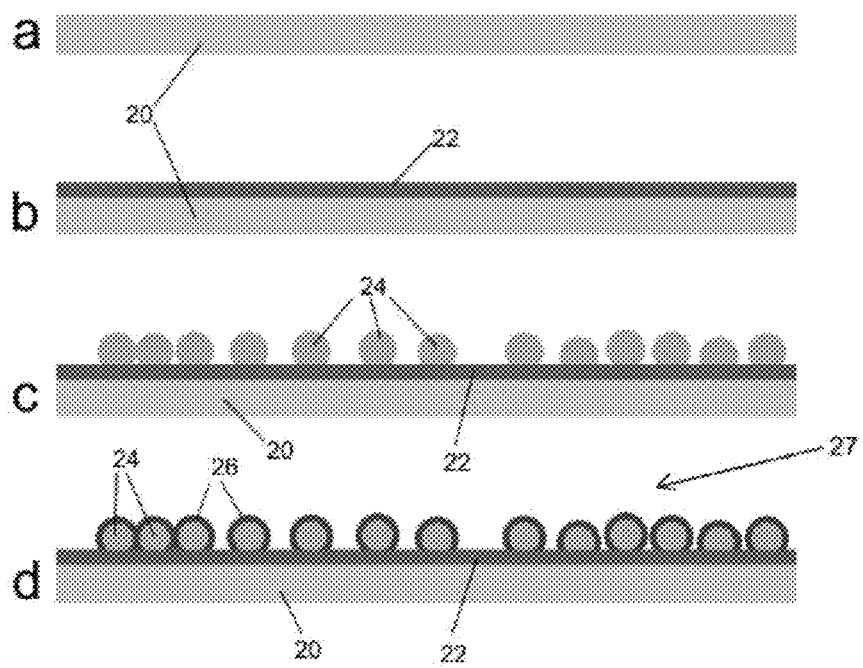
FIG. 2 depicts a manufacturing process of a sensor element according to an embodiment of the invention and which can be used in the Raman spectrometer of FIG. 1.

Manufacturing steps of a sensor element according to an embodiment of the invention including carrier is shown in FIG. 2. In FIG. 2, four steps denoted with a-d are shown. In step a), a carrier 20 is shown in cross sectional view. The carrier is cleaned to remove organic substances and an intermediate layer 22 is deposited on top of the carrier as shown in step b). The intermediate layer can be omitted, but may aid in adhering the active surface to the carrier.

On top of the intermediate layer, metal colloids 24 of which a few are referred to by a reference numeral in step c) are provided. The colloids themselves, which may have a smooth surface, form an active surface by their nature, which can be increased by their mutual orientation. Alternatively, the material may be deposited as a single layer which is roughened at a later stadium, e.g. electrochemically. It is further possible that nanostructures such as nanowires are provided on a carrier thereby forming an active surface (see for instance US 2008/0285024). A commercially available SERS active surface is Klarite™, a sensor element based on a gold substrate, available from Renishaw Diagnostics Ltd.

Finally in step d), the top surface of the sensor element including the active surface is coated with a thin layer of inert material 26. The active surface is now encapsulated by the carrier and the layer of material so that the active surface can not react with the analyte, 27 e.g. bond, adhere, adsorb. The analyte 27 can be contacted with the sensor element as indicated by the arrow shown in FIG. 2.

Figure 3:
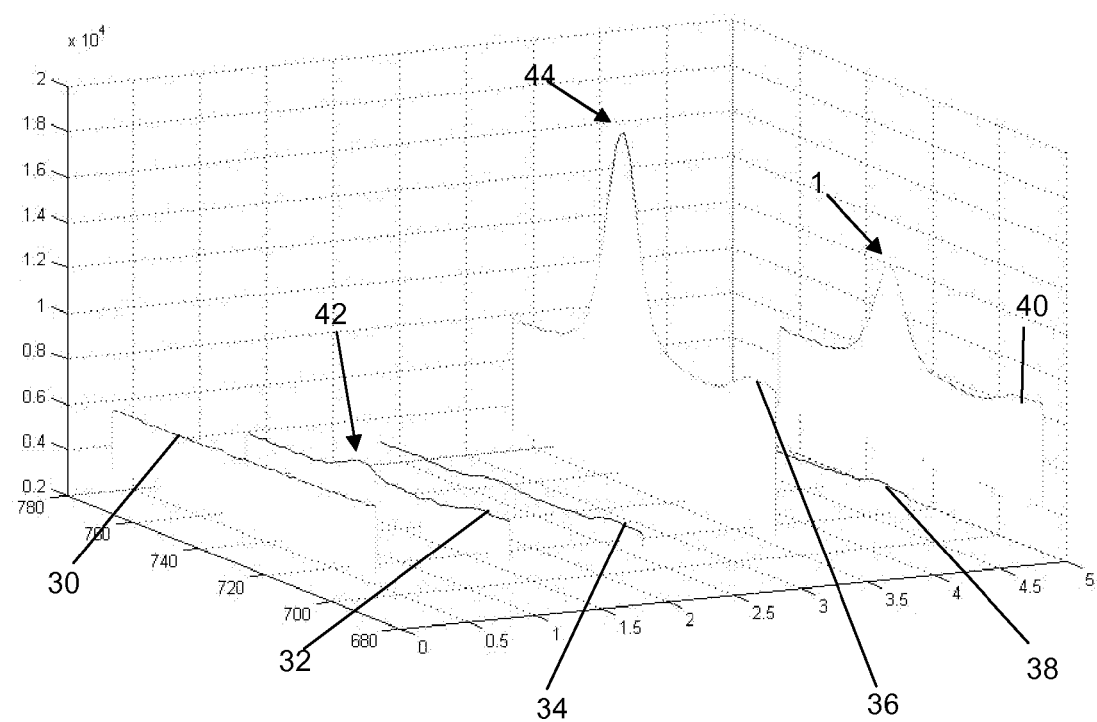
FIG. 3 depicts a measurement result of a sensor element according to an embodiment of the invention, showing that the sensor element can be used multiple times sequentially.

FIG. 3 depicts measurement results using a sensor element according to an embodiment of the invention. Shown are six graphs 30, 32, 34, 36, 38, 40 of subsequent measurements. Each graph depicts the intensity of Raman scattering for a given frequency shift in a certain frequency range.

For graph 30, the sensor element was submerged in DI (deionised) water, which shows a flat signal in this particular frequency range. In graph 32, the sensor element was in contact with an adenine solution in DI water, wherein the adenine is the analyte is in this case. As a result of this, an increase in intensity is shown for a particular frequency band as indicated by arrow 42. Subsequently, the sensor element is rinsed and submerged in DI water again. The measurement result is shown in graph 34 and a flat signal is again the result.

Graph 36 shows the measurement result of the sensor element in contact with another solution of adenine having a higher concentration. The increase in intensity belonging to the adenine can now be more clearly seen as indicated by arrow 44. Graph 38 shows again the measurement result of the sensor element being in contact with DI water after rinsing the sensor element and shows that there is a flat signal again.

In the last graph 40, the sensor element is in contact with a adenine solution again, and the corresponding measurement signal is shown again.

These experiments show that the sensor element according to the invention is able to perform multiple measurements after one another and that both qualitative and quantitative measurement results can be obtained with the use of the coated surface enhanced Raman scattering sensor element.

The invention claimed is:

1. A Raman spectrometer comprising a light source, a sensor element and a detector, wherein the spectrometer is in combination with a sample to be analysed comprising at least one analyte, wherein the sensor element comprises an active surface, which active surface is coated with a layer of inert material to be placed in contact with a sample to be analysed, wherein the layer of inert material, which is inert to the at least one analyte, coats the active surface, thereby preventing the at least one analyte from direct or indirect binding, adhering, or adsorbing to the active surface.

2. The Raman spectrometer according to claim 1, wherein the layer of inert material comprises one or more materials selected from the group consisting of carnauba wax, ethyl cellulose, ethylene maleic anhydride copolymer, methyl vinyl ether, octadecyl vinyl ether, phenoxy resin, poly 2-ethylhexyl methacrylate, poly (caprolactone), poly (caprolactone) triol, polybutadiene, poly-n-butyl acrylate, poly-p-vinyl phenol, polybutadiene oxide, polybutadiene hydroxy terminated, polybutadiene-methylacrylated, polybutadiene acrylonitrile, polydecyl acetate, polyethyl acrylate, polyethylene, polyethylene glycol methyl ether, polyethylene glycol, polyhexyl methacrylate, poly-1-butene, polymethacrylate, polystyrene, polyvinyl butyryl, polyvinyl carbazone, polyvinyl chloride, polyvinyl isobutyl ether, polyvinyl methyl ether, polyvinyl stearate, vinyl alcohol/vinyl acetate copolymer and fluorinated polymers.

3. The Raman spectrometer according to claim 1, wherein the layer of inert material forms a dynamic coating on the active surface.

4. The Raman spectrometer according to claim 1, wherein the active surface comprises silver, gold, platinum, palladium, cobalt, copper and/or graphene.

5. The Raman spectrometer according to claim 1, wherein the active surface comprises roughness features.

6. The Raman spectrometer according to claim 1, wherein the active surface is encapsulated by the inert material.

7. The Raman spectrometer according to claim 1, wherein the layer of inert material has a thickness of less than 50 nm.

8. The Raman spectrometer according to claim 1, further comprising an optical system to collect surface enhanced Raman scattering and direct it to the detector.

9. The Raman spectrometer according to claim 1, further comprising an optical system to direct monochromatic light from the light source to the sensor element.

10. The Raman spectrometer according to claim 1, further comprising a filter to filter the light scattered by the analyte and thereby filter out Rayleigh scattering.

11. A sensor element comprising an active surface which is coated with a layer of inert material, wherein said layer is in contact with a sample to be analysed comprising at least one analyte, and wherein the layer of inert material, which is inert to the at least one analyte, coats the active surface, thereby preventing the at least one analyte from direct or indirect binding, adhering, or adsorbing to the active surface.

12. The sensor element according to claim 11, wherein the active surface is encapsulated by inert material.

13. The sensor element according to claim 11, wherein the layer of material comprises one or more materials selected from the group consisting of carnauba wax, ethyl cellulose, ethylene maleic anhydride copolymer, methyl vinyl ether, octadecyl vinyl ether, phenoxy resin, poly 2-ethylhexyl methacrylate, poly (caprolactone), poly (caprolactone) triol, polybutadiene, poly-n-butyl acrylate, poly-p-vinyl phenol, polybutadiene oxide, polybutadiene hydroxy terminated, polybutadiene-methylacrylated, polybutadiene acrylonitrile, polydecyl acetate, polyethyl acrylate, polyethylene, polyethylene glycol methyl ether, polyethylene glycol, polyhexyl methacrylate, poly-1-butene, polymethacrylate, polystyrene, polyvinyl butyryl, polyvinyl carbazone, polyvinyl chloride, polyvinyl isobutyl ether, polyvinyl methyl ether, polyvinyl stearate, vinyl alcohol/vinyl acetate copolymer and fluorinated polymers.

14. The sensor element according to claim 11, wherein the layer of inert material forms a dynamic coating on the active surface.

15. The sensor element according to claim 11, further comprising a carrier on which the active surface is located.

16. The sensor element according to claim 15, wherein the active surface has roughness features.

17. The sensor element according to claim 15, wherein the carrier is selected from the group consisting of glass, silica, silicon and light-conducting fibres.

18. The sensor element according to claim 15, wherein the active surface is provided on the intermediate layer.

19. The sensor element according to claim 11, wherein the active surface comprises at least one material selected from the group consisting of: gold, silver, copper, platinum, palladium and graphene.

20. A method for manufacturing a sensor element and contacting therewith a sample to be analysed, said method comprising the steps:
a) providing an active surface;
b) coating the active surface with a layer of inert material; and
c) contacting said layer with a sample to be analysed comprising at least one analyte, wherein the layer of inert material, which is inert to the at least one analyte, coats the active surface, thereby preventing the at least one analyte from direct or indirect binding, adhering, or adsorbing to the active surface.

21. The method according to claim 20, further comprising: providing a carrier, wherein the active surface is provided on the carrier.

22. The method according to claim 21, further comprising: covering the carrier with an intermediate layer, wherein the intermediate layer aids in adhering the active surface to the carrier.

23. A method for obtaining the Raman spectrum of an analyte using a sensor element comprising an active surface which is coated with a layer of inert material, comprising the following steps:
a) providing a sensor element, comprising an active surface which is coated with a layer of inert material and placing the layer of inert material in contact with a sample to be analysed comprising at least one analyte, wherein the layer of inert material, which is inert to the at least one analyte, coats the active surface, thereby preventing the at least one analyte from direct or indirect binding, adhering, or adsorbing to the active surface;
b) illuminating the sensor element with monochromatic light; and
c) detecting surface enhanced Raman scattering by the sensor element.

24. The Raman spectrometer according to claim 3, wherein the layer of inert material forms a dynamic coating on the active surface via a binding unit.

25. The Raman spectrometer according to claim 24, wherein the layer of inert material forms the dynamic coating on the active surface via a thiol or amine binding unit.

26. The Raman spectrometer according to claim 25, wherein the layer of inert material is immobilized to the active surface.

27. The Raman spectrometer according to claim 5, wherein the active surface roughness features are in the range of 1-1000 nm.

28. The Raman spectrometer according to claim 1, wherein the layer of inert material has a thickness from 0.1 to 20 nm.

29. The Raman spectrometer according to claim 1, wherein the layer of inert material has a thickness from 0.1 to 5 nm.

30. The sensor element according to claim 14, wherein the layer of inert material forms a dynamic coating on the active surface via a binding unit.

31. The sensor element according to claim 30, wherein the layer of inert material forms the dynamic coating on the active surface via a thiol or amine binding unit.

32. The sensor element according to claim 31, wherein the layer of inert material is immobilized to the active surface.

33. The sensor element according to claim 16, wherein the active surface roughness features are in the range of 1-1000 nm.

34. The sensor element according to claim 18, wherein the intermediate layer comprises amino and alkoxysilane moieties.

35. The sensor element according to claim 11, wherein the sensor element is for Raman spectroscopy.

36. The sensor element according to claim 11, wherein the sensor element is for Surface Enhanced Fluorescence.

37. The method according to claim 23, wherein the method is for dynamic measurements.

38. A method for obtaining the Surface Enhanced Fluorescence of an analyte using a sensor element comprising an active surface which is coated with a layer of inert material, comprising the following steps:
a) providing a sensor element, comprising an active surface which is coated with a layer of inert material and placing the layer of inert material in contact with a sample to be analysed comprising at least one analyte, wherein the layer of inert material, which is inert to the at least one analyte, coats the active surface, thereby preventing the at least one analyte from direct or indirect binding, adhering, or adsorbing to the active surface;

b) illuminating the sensor element with monochromatic light; and c) detecting Surface Enhanced Fluorescence by the sensor element.

39. The method according to claim 38, wherein the method is for dynamic measurements.

* * * * *